US00PP15233P2

(12) United States Plant Patent
Van Haaster

(10) Patent No.: US PP15,233 P2
(45) Date of Patent: Oct. 12, 2004

(54) ***DAHLIA* PLANT NAMED 'SABINAS'**

(50) Latin Name: *Dahlia variabilis*
Varietal Denomination: Sabinas

(76) Inventor: Johanna G. H. Van Haaster, P.O. Box 26, 2678 ZG De Lier (NL)

( * ) Notice: Subject to any disclaimer, the term of this patent is extended or adjusted under 35 U.S.C. 154(b) by 0 days.

(21) Appl. No.: 10/698,677

(22) Filed: Oct. 31, 2003

(51) Int. Cl.[7] ..... A01H 5/00

(52) U.S. Cl. ..... Plt./321
(58) Field of Search ..... Plt./321

*Primary Examiner*—Kent Bell
(74) *Attorney, Agent, or Firm*—Mark P. Bourgeois

(57) ABSTRACT

A new cultivar of *Dahlia* plant named 'Sabinas' that is characterized by a short crop time of 6 to 7 weeks, a compact, upright and uniform growth habit, basal branching, a large quantity of small bicolored inflorescences that have a golden center and change to orange toward the ray floret apex. In combination, these traits set 'Sabinas' apart from all other existing varieties of *Dahlia* known to the inventor.

1 Drawing Sheet

Botanical classification: *Dahlia variabilis.*
Variety denomination: 'Sabinas'.

BACKGROUND OF THE INVENTION

The present invention relates to a new and distinct cultivar of *Dahlia* plant botanically known as *Dahlia variabilis* and hereinafter referred to by the cultivar name 'Sabinas'.

The new cultivar is the product of a breeding program conducted by the inventor in a cultivated area of Hillegom, The Netherlands. The objective of the breeding program is to develop new *Dahlia* cultivars with interesting and unique inflorescence and foliage colors.

'Sabinas' is a hybrid that originated from the induced hybridization of the female or seed parent an unidentified proprietary *Dahlia variabilis* seedling selection (not patented) and the male or pollen parent an unidentified proprietary *Dahlia variabilis* seedling selection (not patented). The cultivar 'Sabinas' was selected by the inventor in 1996 as a single parent within the progeny of the stated cross in a controlled environment of Hillegom, The Netherlands.

Asexual reproduction by terminal cuttings of the new cultivar 'Sabinas' were taken in 1999 in Hillegom, The Netherlands by the inventor. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dahlia* cultivar 'Sabinas'. These traits in combination distinguish 'Sabinas' as a new and distinct cultivar apart from all other existing varieties of *Dahlia* known to the inventor.

1. *Dahlia* 'Sabinas' has a short crop time of 6 to 7 weeks.
2. *Dahlia* 'Sabinas' exhibits an upright and uniform growth habit.
3. *Dahlia* 'Sabinas' exhibits basal branching.
4. *Dahlia* 'Sabinas' exhibits a compact growth habit.
5. *Dahlia* 'Sabinas' exhibits a large quantity of small inflorescences.

6. *Dahlia* 'Sabinas' exhibits bicolored inflorescences that have a golden center and change to orange toward the ray floret apex.

Plants of the new *Dahlia* 'Sabinas' are different than the parent plants primarily in ray floret color.

The closest comparison variety is *Dahlia* 'Fuerte' (U.S. Plant Pat. No. 12,814). 'Sabinas' is different than 'Fuentes' in having a longer crop time, a more compact habit, less vigor and bicolored inflorescences that have a golden center and change to orange toward the ray floret apex.

BRIEF DESCRIPTION OF THE DRAWING

The accompanying photograph illustrates the distinguishing traits of *Dahlia* 'Sabinas'. The plant in the photograph shows an overall view of a 8 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dahlia* cultivar named 'Sabinas'. Data was collected in Maasland, The Netherlands from 8 week glass greenhouse grown plants in 10.5 cm diameter containers. The time of year was June and the temperature was kept at 17° Centigrade during the day and night. The light level was natural outdoor light plus supplementary light of 3600 lux during the day and there were no photoperiodic treatments. Dazide growth retardant was used 4 times at a rate of 2 grams per liter. Color determinations are in accordance with The Royal Horticultural Society Colour Chart 2001 edition, except where general color terms of ordinary dictionary significance are used. The growing requirements are similar to the species.

'Sabinas' has not been tested under all possible conditions and phenotypic differences may be observed with variations in environmental, climatic, and cultural conditions, however, without any variance in genotype.

Botanical classification: *Dahlia* 'Sabinas'.
Use: Ornamental.

Parentage: 'Sabinas' is a hybrid plant that resulted from the induced hybridization of the following parent plants.

*Female parent.*—An unidentified proprietary *Dahlia variabilis* seedling selection.

*Male parent.*—An unidentified proprietary *Dahlia variabilis* seedling selection.

Vigor: Low.

Growth rate: Approximately 5 cm. per month.

Growth habit: Upright.

Plant shape: Globose.

Suitable container size: 12 cm container.

Height: 18 cm. in height.

Width: 22 cm. in width.

Hardiness: USDA Zone 8.

Propagation: Terminal cuttings.

Time to initiate roots: Approximately 5 to 8 days to produce roots on an initial cutting.

Time to produce a rooted cutting or liner: Approximately 12–16 days.

Crop time: From a rooted cutting, approximately 6 to 7 weeks are required to produce a finished flowering plant.

Root system: Fine and fibrous.

Stem:

*Branching habit.*—Free branching.

*Average number of lateral branches.*—10.

*Pinching.*—Yes.

*Lateral branch diameter.*—5 mm. in diameter.

*Lateral branch length.*—13 cm. in length.

*Lateral branch strength.*—High.

*Stem color* (*immature*).—144A.

*Stem color* (*mature*).—199B.

*Pubescence.*—Slight.

*Internode length.*—1.5 cm. between nodes.

*Shape.*—Round.

*Surface.*—Smooth, glossy.

Foliage:

*Texture.*—Slightly glossy.

*Leaf arrangement.*—Opposite.

*Compound or single.*—Single, upper leaves compound.

*Quantity of leaves per lateral branch.*—10.

*Quantity of leaflets per leaf.*—3 on upper leaves only.

*Leaflet shape.*—Broad ovate.

*Leaflet apex.*—Acute.

*Leaflet base.*—Attenuate.

*Single leaf length.*—4.8 cm. in length.

*Single leaf width.*—3.4 cm. in width.

*Leaflet length.*—3.1 cm. in length.

*Leaflet width.*—2.0 cm. in width.

*Pubescence.*—Slight.

*Leaflet margin.*—Serrate.

*Vein pattern.*—Pinnate.

*Young leaf color* (*lower surface*).—191A.

*Young leaf color* (*upper surface*).—147A.

*Mature leaf color* (*lower surface*).—191A.

*Mature leaf color* (*upper surface*).—137A.

*Vein color* (*lower surface*).—138A.

*Vein color* (*upper surface*).—138A.

*Leaf attachment.*—Petiolate.

*Petiole dimensions.*—2.2 cm in length and 2.0 mm. in width.

*Petiole color.*—143A.

Inflorescence:

*Inflorescence type.*—Terminal capitulum.

*Flowering habit.*—Continuous.

*Quantity of inflorescences per capitula.*—23 ray florets and 43 disc florets.

*Quantity of inflorescences per lateral stem.*—Approximately 2 capitula.

*Quantity of inflorescence buds per lateral stem.*—Approximately 4 capitula.

*Quantity of inflorescences and buds per plant.*—Approximately 20 capitula.

*Flowering season.*—Summer.

*Rate of inflorescence opening.*—In a capitula, approximately 25% of the flowers are opened at once.

*Fragrance.*—None.

*Bud length.*—7 mm. in length.

*Bud diameter.*—9 mm. in diameter.

*Bud shape.*—Globose.

*Bud color.*—144A with a green base 143B and a yellow-green top 151B.

*Inflorescence aspect.*—Upright to outward/upright.

*Inflorescence shape.*—Ray florets with disc florets massed at the center.

*Inflorescence dimensions.*—5.0 cm. in diameter and 1.3 cm. in height.

*Inflorescence longevity.*—Lasts approximately 14 days on plant.

*Ray floret appearance.*—Dull.

*Ray floret texture.*—Smooth.

*Ray floret fused or unfused.*—Unfused.

*Ray floret shape.*—Oblanceolate.

*Ray floret margin.*—Entire.

*Ray floret apex.*—Obtuse to slightly praemorse.

*Ray floret base.*—Cuneate.

*Ray floret dimensions.*—1.9 cm. in length, 9 mm. in width.

*Ray floret color when opening* (*upper side*).—1A with orange-red tips 30A.

*Ray floret color when opening* (*under side*).—1A with orange-red tips 30A.

*Ray floret color fully open* (*upper side*).—30A with base yellow 7B.

*Ray floret color fully open* (*under side*).—30A with base yellow 1B.

*Ray floret color fading.*—164B.

*Disc floret appearance.*—Dull.

*Disc floret texture.*—Smooth.

*Disc floret fused or unfused.*—Lower ⅘ fused.

*Disc floret shape.*—Trumpet shaped.

*Disc floret margin.*—Entire.

*Disc floret apex.*—Acute.

*Disc floret dimensions.*—4 mm. in length, 1.2 mm. in width.

*Entire disc diameter.*—Approximately 1 cm.

*Disc floret color when opening* (*upper side*).—17C.

*Disc floret color when opening* (*under side*).—17C.

*Disc floret color fully open* (*upper side*).—17C.

*Disc floret color fully open* (*under side*).—17C.

*Disc floret color fading.*—Not fading.

Self-cleaning or persistent: Persistent.

Phyllaries:

*Arrangement.*—Under each floret is one phyllary.

*Color immature* (*upper side*).—150D.

*Color immature* (*under side*).—150D.

*Color mature* (*upper side*).—150D.

*Color mature* (*under side*).—150D.

*Shape.*—Oblong.

*Margin.*—Entire.

*Apex.*—Acute.

*Base.*—Cuneate.

*Dimensions.*—1.0 cm. in length and 3 mm. in width.

Secondary phyllaries:
*Quantity.*—5.
*Length.*—9 mm.
*Width.*—4 mm.
*Shape.*—Obovate.
*Base.*—Cuneate.
*Apex.*—Acute.
*Margin.*—Entire.
*Color.*—137A both surfaces.

Peduncle:
*Peduncle dimensions.*—6.2 cm. in length and 1.5 mm. in diameter.
*Peduncle angle.*—0°.
*Peduncle color.*—143B.
*Peduncle strength.*—Strong.

Reproductive organs:
*Androecium.*—Present on disc florets only.
*Gynoecium.*—Present on both ray and disc florets.
*Stamen number.*—5 on disc florets only.
*Stamen length.*—3 mm.
*Anther shape.*—Basifixed, narrow oblong.
*Anther dimensions.*—2 mm. in length.
*Anther color.*—17B.
*Filament length.*—1 mm.
*Filament color.*—145C.
*Amount of pollen.*—Low.
*Pollen color.*—17B.
*Pistil number.*—1 in number.
*Pistil dimensions.*—1.2 cm. in length.
*Stigma shape.*—Cleft.
*Stigma color.*—17C.
*Style length.*—9 mm.
*Style color.*—154B.
*Ovary color.*—145A.

Seed: Seed production has not been observed.

Disease resistance: Plants of the new *dahlia* have not been observed for disease resistance.

Pest resistance: Plants of the new *dahlia* have not been observed for pest resistance.

I claim:

1. A new and distinct variety of *Dahlia* plant named 'Sabinas' as described and illustrated.

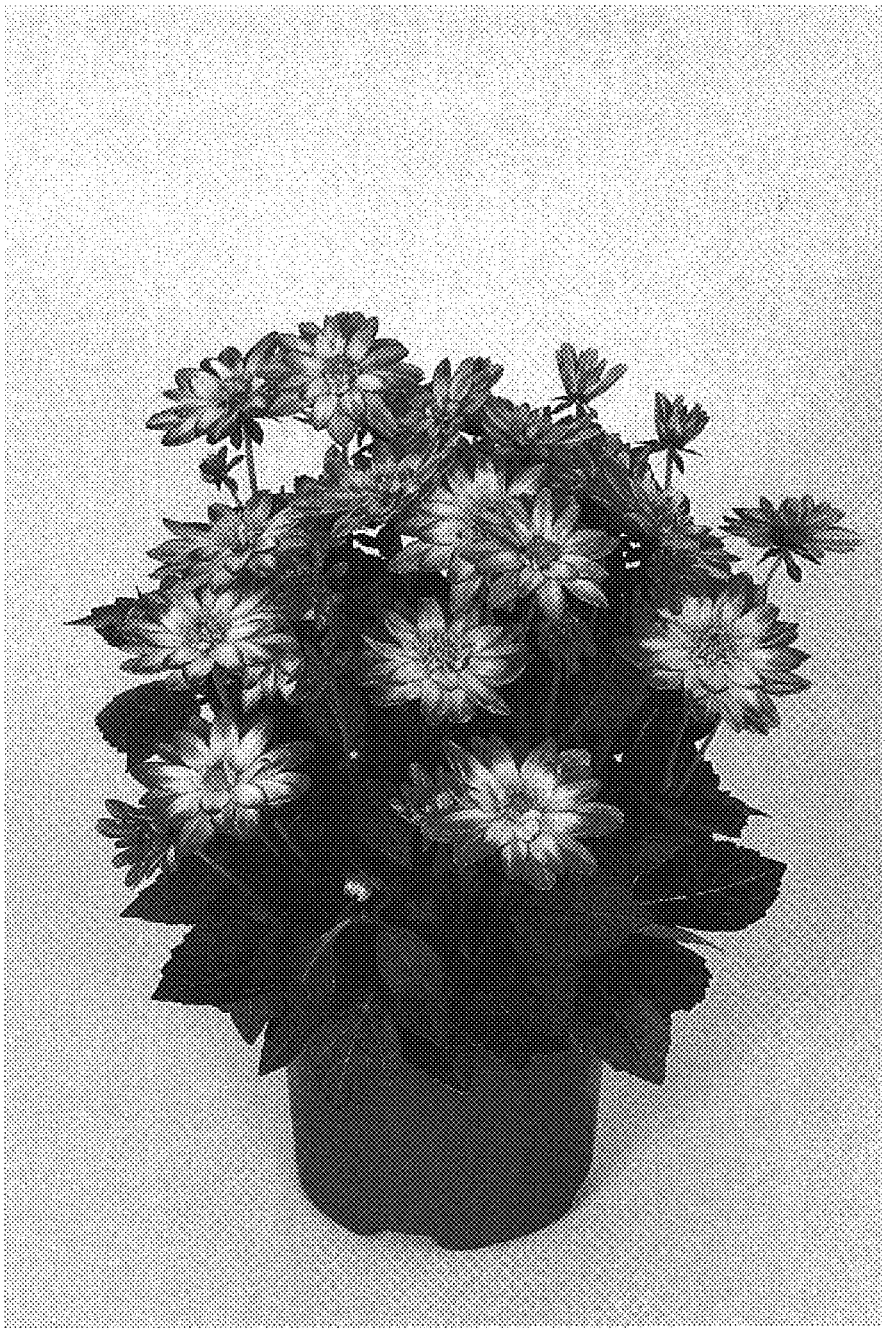

* * * * *